(12) United States Patent
Van Beelen

(10) Patent No.: US 10,604,780 B2
(45) Date of Patent: Mar. 31, 2020

(54) LOW GLUTEN YEAST HYDROLYSATES

(71) Applicant: DSM IP ASSETS B.V., Heerlen (NL)

(72) Inventor: Petrus Norbertus Van Beelen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 408 days.

(21) Appl. No.: 15/321,530

(22) PCT Filed: Jun. 26, 2015

(86) PCT No.: PCT/EP2015/064483
§ 371 (c)(1),
(2) Date: Dec. 22, 2016

(87) PCT Pub. No.: WO2016/001072
PCT Pub. Date: Jan. 7, 2016

(65) Prior Publication Data
US 2017/0152542 A1   Jun. 1, 2017

(30) Foreign Application Priority Data

Jul. 1, 2014  (EP) .................. 14175235

(51) Int. Cl.
| | | |
|---|---|---|
| C12P 21/06 | (2006.01) | |
| A23L 27/24 | (2016.01) | |
| A23L 33/145 | (2016.01) | |
| A23J 3/34 | (2006.01) | |
| C12N 9/62 | (2006.01) | |

(52) U.S. Cl.
CPC ............... C12P 21/06 (2013.01); A23J 3/347 (2013.01); A23L 27/24 (2016.08); A23L 33/145 (2016.08); C12N 9/62 (2013.01); C12Y 304/21026 (2013.01); *A23V 2002/00* (2013.01)

(58) Field of Classification Search
CPC .................................. C12P 21/06; A23L 27/24
See application file for complete search history.

(56) References Cited

U.S. PATENT DOCUMENTS

| | | |
|---|---|---|
| 8,084,068 B2 | 12/2011 | Noordam et al. |
| 8,257,760 B2 | 9/2012 | Edens et al. |
| 8,524,225 B2 | 9/2013 | Edens et al. |
| 9,192,184 B2 | 11/2015 | Noordam |
| 2008/0003327 A1 | 1/2008 | Pasternack et al. |

FOREIGN PATENT DOCUMENTS

| | | |
|---|---|---|
| CN | 1659271 A | 8/2005 |
| CN | 101686720 A | 3/2010 |
| WO | 03104382 A1 | 12/2003 |
| WO | 2005027953 A2 | 3/2005 |
| WO | 2005067734 A2 | 7/2005 |
| WO | 2009007424 A1 | 1/2009 |
| WO | 2012110534 A1 | 8/2012 |

OTHER PUBLICATIONS https://www.glutenfreewatchdog.org/news/ (Year: 2014).*
https://www.glutenfreedietitian/is-marmite-gluten-free/ (Year: 2011).*
Stepniak et al., Highly efficient gluten degradation with a newly identified prolyl endoprotease implications for celiac disease. American Journal of Physiology Gastrointestinal Liver Physiology, G621-G629, vol. 291. (Year: 2006).*
International Search Report of International Application No. PCT/EP2015/064483 dated Aug. 27, 2015.

* cited by examiner

*Primary Examiner* — Taeyoon Kim
*Assistant Examiner* — Tiffany M Gough
(74) *Attorney, Agent, or Firm* — McBee Moore & Vanik IP, LLC

(57) ABSTRACT

The present invention relates to a process for preparing a yeast hydrolysate comprising less than 100 ppm gluten and at least 1 ppm gluten based on salt-free yeast dry matter.

13 Claims, No Drawings

LOW GLUTEN YEAST HYDROLYSATES

CROSS-REFERENCE TO RELATED APPLICATIONS

This application is a National Stage entry of International Application No. PCT/EP2015/064483 filed 26 Jun. 2015 which claims priority to European Patent Applications No. 14175235.2, filed 01 Jul. 2014.

FIELD OF THE INVENTION

The present invention relates to low gluten yeast hydrolysates and a process for the for producing the same using a prolyl-specific endoprotease.

BACKGROUND OF THE INVENTION

For the production of yeast extract, typically baker's and torula yeast cells may be subjected to autolysis. Some sources of yeast (e.g. spent brewer's yeast) contain residues of gluten (gliadins). As a consequence, extracts and suspensions derived of yeasts sources containing gliadins have limited use in food applications due to the intolerance towards gliadins in part of the population (Celiac disease). It was observed that typical yeast extracts or autolysates obtained from sources containing gliadins (e.g. brewer's yeast extracts) contain gliadins in a concentration exceeding the acceptable threshold of 20 ppm by weight.

Reduction of gliadins from yeast sources containing gliadins enables the use of these yeasts and extracts thereof is food applications which require absence of low concentrations of gluten.

A problem with the reduction of gliadins in yeast is to reduce specifically the gliadin content without undesired side effects of the treatment. For example, it is undesired that the treatment aiming to reduce the gliadin content also degrades the yeast' RNA.

It was now surprisingly found that gliadins can be removed from a yeast source containing gliadins by incubation with a proline-specific endoprotease during the hydrolysis and/or autolysis process. It was surprisingly found that the gliadins can effectively be hydrolyzed to a level below 20 ppm by weight on dry matter content of the yeast autolysates and extracts. Further, it was found that incubation with a proline-specific endoprotease during the hydrolysis and/or autolysis process did not degrade the RNA present in the yeast.

DEFINITIONS

"Yeast" is defined herein as a solid, paste or liquid composition comprising yeast cells. Preferably the yeast cells are from the genus *Saccharomyces*. The yeast may be produced in a fermentation process such as a process for the production common baker's yeast. Preferably the yeast is a brewer's yeast, such as a spent brewer's yeast that may be obtained as a side stream from beer brewing processes.

"Autolysis" is defined herein as the enzymatic breakdown of yeast cells using endogenous yeast enzymes and optionally exogenous added enzymes. Autolysis may result in both a yeast autolysate and a yeast extract (see definitions below).

"Hydrolysis" is defined herein as the enzymatic breakdown of yeast cells using only exogenous enzymes. The endogenous yeast enzymes are first inactivated for instance by a heat shock. Hydrolysis may also result in both a yeast autolysate and a yeast extract (see definitions below).

"Yeast hydrolysate" is defined herein as the digest of yeast, such as a spent brewer's yeast, obtained by autolysis or hydrolysis as defined herein before and resulting in a yeast autolysate or a yeast extract as defined herein below.

"Yeast autolysate" is the concentrated, not extracted, partially soluble digest obtained from brewer's yeast cells, preferably spent brewer's yeast cells. Digestion is accomplished by hydrolysis or autolysis of yeast cells as defined hereinbefore. Brewer's yeast autolysate contains both soluble and insoluble components derived from the whole yeast cell (e.g. Food Chemical Codex).

"Yeast extract" comprises only the water soluble components of the brewer's yeast cell, the composition of which is primarily amino-acids, peptides, carbohydrates and salts. Yeast Extract is produced through the hydrolysis of peptide bonds by the naturally occurring enzymes present in edible yeast and/or or by the addition of food-grade enzymes (Food Chemical Codex), i.e. by autolysis and/or hydrolysis as defined hereinbefore.

"Protease" is defined herein as a hydrolase acting on peptide bonds in a protein substrate in an endo-fashion, i.e. cleaving the peptide bonds anywhere in the polypeptide chain in contrast to a (exo)peptidase which is defined herein as a hydrolase acting on peptide bonds in a protein substrate in an exo fashion, i.e. acting near the ends of the polypeptide chain: aminopeptidases are cleaving off amino acids, di- tri or higher oligopeptides from the N-terminal side of the polypeptide chain and carboxypeptidases cleaving off amino acids, di- tri or higher oligopeptides form the C-terminal side of the polypeptide chain. The endoproteases are divided into subclasses on the basis of their catalytic mechanism: serine endoproteases (EC 3.4.21.xx) cysteine endoproteases (EC 3.4.22.xx) aspartic endoproteases (EC 3.4.23.xx) and metallo-endoproteases (EC 3.4.24.xx).

A "proline-specific endoprotease" is defined herein as an endoprotease cleaving protein or oligopeptides substrates at the C-terminal side of a proline residue in the protein or oligopeptides substrate. The proline-specific endoprotease has been classified as EC 3.4.21.26. The enzyme can be obtained from various sources such as mammalian sources, bacteria (e.f. *Flavobacterium*) and fungi (*Aspergillus*, in particular *Aspergillus niger*). The enzyme of *Aspergillus niger* has been described in detail in WO02/45524, WO02/46381, WO03/104382. A suitable fungal enzyme from *Penicillium chrysogenum* is disclosed in WO2009/144269. A suitable bacterial enzyme from *Flavobacterium meningosepticum* is disclosed in WO03068170.

"Gluten" is defined herein as a protein composite found in grains and is subdivided in gliadin and glutenin proteins.

DETAILED DESCRIPTION OF A PREFERRED EMBODIMENT

In a first aspect, the invention provides a process for preparing a yeast hydrolysate characterized in that the process comprises the step of contacting a gluten containing yeast hydrolysate with a proline-specific endoprotease resulting in a yeast hydrolysate comprising less than 100 ppm gluten, or gliadin, based on salt-free yeast dry matter. Preferably, the resulting yeast hydrolysate is comprising less than 50 ppm gluten, or gliadin, more preferably less than 40 ppm, more preferably less than 30 ppm and more preferably less than 20 ppm gluten, or gliadin, based on salt-free yeast dry matter. The yeast hydrolysate preferably may contain at least 5 ppm gluten, or gliadin, more preferably at least 4 ppm gluten, or gliadin, more preferably at least 3 ppm gluten, or gliadin, more preferably at least 2 ppm gluten, or gliadin.

Most preferably the yeast hydrolysate contains at least 1 ppm gluten based on salt-free yeast dry matter. The inventors of the present invention surprisingly found that the present proline-specific endoprotease provides a low gluten yeast hydrolysate wherein the yeast' RNA or derived 5'ribonucleotides is not, or not substantially, degraded and thus available for the conversion to taste enhancing 5'-ribonucleotides.

Any proline-specific endoprotease can be used in the process of the invention. The proline-specific endoprotease may be of mammalian, plant or microbial origin. Suitable microbial proline-specific endoproteases are from bacteria such as *Flavobacterium meningosepticum* or from fungi such as *Penicillium chrysogenum* or *Aspergillus niger*. In a preferred embodiment, the process of the invention is using the proline-specific endoprotease of *Aspergillus niger*. This enzyme is commercially available as Brewer's Clarex and may be obtained from DSM Food Specialties, Delft, The Netherlands.

The conditions for the step wherein the proline-specific endoprotease is used to reduce the gluten content of the yeast hydrolysate, such as pH and temperature, may vary from proline-specific endoprotease to proline-specific endoprotease but may be selected by the skilled person without undue burden, based on the enzymatic properties that are known in the art for the various proline-specific endoproteases.

Preferably, the amount of proline-specific endoprotease which is contacted with the present gluten containing yeast hydrolysate is within the range of more than zero to 0.5% w/w on salt free yeast dry matter. More preferably the amount of proline-specific endoprotease which is contacted with the present gluten containing yeast hydrolysate is within the range of 0.01 to 0.5, more preferably within the range of 0.02 to 0.1 or to 0.01 w/w on salt free yeast dry matter.

The yeast hydrolysate may be a yeast extract or yeast autolysate as defined hereinbefore. The yeast may be any suitable yeast and is preferable selected from the genera *Saccharomyces, Brettanomyces, Kluyveromyces, Candida* or *Torula*, preferably the genus *Saccharomyces*, more preferably *Saccharomyces cerevisiae* as is used as a baker's yeast or the brewer's yeast *Saccharomyces carlsbergensis* or its synonym *Saccharomyces pastorianus* as is used in the brewing industry for instance to produce lager beer. In a preferred embodiment the yeast is a brewer's yeast and more preferably a spent brewer's yeast which is a side product of the beer brewing process.

The yeast hydrolysate may be produced from yeast cells by methods well known in the art, such as by autolysis or hydrolysis as defined hereinbefore. The yeast cells may contain gluten for instance because in the production process for the yeast a raw material containing gluten is used. In particular brewer's yeast, more preferably spent brewer's yeast, may contain residual gluten from the barley or wheat used in the beer brewing process.

In the process of the invention a yeast hydrolysate is prepared comprising less than 100 ppm gluten, or gliadin, based on salt-free yeast dry matter. Preferably, the resulting yeast hydrolysate is comprising less than 50 ppm gluten, or gliadin, more preferably less than 40 ppm, more preferably less than 30 ppm and more preferably less than 20 ppm gluten, or gliadin, based on salt-free yeast dry matter. The proline-specific endoprotease used in the process is reducing the amount of gluten present in the yeast hydrolysate by cleaving the gluten with the specificity as described hereinbefore for the proline-specific endoprotease. The skilled person will easily understand that in order to obtain a yeast hydrolysate with less than 100 ppm gluten, the yeast hydrolysate subjected to the step with proline-specific endoprotease must contain more than 100 ppm otherwise, the proline-specific endoprotease is not able to reduce the gluten content. Likewise, in order to obtain a yeast hydrolysate with less than 50 ppm gluten, the yeast hydrolysate subjected to the step with proline-specific endoprotease must contain more than 50 ppm and also in order to obtain a yeast hydrolysate with less than 40 ppm gluten, the yeast hydrolysate subjected to the step with proline-specific endoprotease must contain more than 40 ppm and also in order to obtain a yeast hydrolysate with less than 30 ppm gluten, the yeast hydrolysate subjected to the step with proline-specific endoprotease must contain more than 30 ppm and also in order to obtain a yeast hydrolysate with less than 20 ppm gluten, the yeast hydrolysate subjected to the step with proline-specific endoprotease must contain more than 20 ppm. In general, the yeast hydrolysate subjected to the step with proline-specific endoprotease must contain more gluten than the yeast hydrolysate obtained after the step wherein the proline-specific endoprotease is reducing the gluten content.

It is further preferred to include in the present step of contacting a gluten containing yeast hydrolysate with a proline-specific endoprotease resulting in a yeast hydrolysate comprising less than 100 ppm gluten and at least 1 ppm gluten based on salt-free yeast dry matter also a phosphodiesterase to produce 5'-ribonucleotides and optionally an enzymatic treatment to convert 5'-AMP into 5'-IMP. The advantage of using a combination of a phosphodiesterase with the present proline-specific endoprotease is that a low gluten yeast hydrolysate is obtained with increased amounts of 5'-ribonucleotides.

In a second aspect the invention provides a yeast hydrolysate comprising less than 100 ppm gluten, or gliadin, based on salt-free yeast dry matter. Preferably, the resulting yeast hydrolysate is comprising less than 50 ppm gluten, or gliadin, more preferably less than 40 ppm, more preferably less than 30 ppm and more preferably less than 20 ppm gluten, or gliadin, based on salt-free yeast dry matter. The yeast hydrolysate preferably may contain at least 5 ppm gluten, more preferably at least 4 ppm gluten, or gliadin, more preferably at least 3 ppm gluten, or gliadin, more preferably at least 2 ppm gluten, or gliadin. Most preferably the yeast hydrolysate contains at least 1 ppm gluten, or gliadin, based on salt-free yeast dry matter. The yeast hydrolysate may be obtainable by any suitable process, but is preferably obtainable by, or obtained by, the process of the first aspect of the invention.

In a preferred embodiment of the first or second aspect, the present yeast hydrolysate further comprises 5'-ribonucleotides. The term "5'-ribonucleotides" is herein intended to refer to either the free 5'-ribonucleotides or salts thereof. 5'-IMP, 5'-GMP are known for their flavour enhancing properties. They are capable of enhancing the savoury and delicious taste in certain types of food. Thus the advantage of the present yeast hydrolysate is that it provides flavour enhancing properties in combination with a low amount of gliadin and/or gluten.

The weight percentage of 5'-ribonucleotides in the yeast hydrolysate of the invention (% w/w) is based on the weight of the NaCl free dry matter of the yeast hydrolysate and is calculated as disodium salt heptahydrate ($2Na.7H_2O$) of 5'-ribonucelotide.

In a further preferred embodiment of the first or second aspect, the present yeast hydrolysate further comprises 5'-GMP (5'-guanine mono phosphate) and/or 5'-IMP (5'-inosine mono phosphate). Preferably, the present yeast hydrolysate comprises more than 60%, preferably more than 70%, more preferably more than 80%, more preferably more than 90%, more preferably more than 95% 5'-GMP and/or 5'-IMP of the amount of 5'-GMP and/or 5'-IMP which could maximally be obtained given the amount of RNA present in the yeast cell the yeast hydrolysate is obtained from.

Preferably, the total amount of 5'-GMP and 5'-IMP in the present yeast hydrolysate is at least 1%, 1.5%, 2%, 2.5%, 3%, 3.5, 4%, 5% or at least 6% based on the NaCl free dry matter of the yeast hydrolysate. If the yeast hydrolysate is a yeast autolysate, the total amount of 5'-GMP and 5'-IMP is at least 1%, 1.5%, 2%, 2.5%, 3%, 3.5, 4%, 5% or at least 6% based on the NaCl free dry matter of the yeast autolysate. If the present yeast hydrolysate is a yeast extract, the total amount of 5'-GMP and 5'-IMP is at least 1%, 1.5%, 2%, 2.5%, 3%, 3.5, 4%, 5% or at least 6% based on the NaCl free dry matter of the yeast extract. Preferably, the total amount of 5'-GMP and 5'-IMP in the present yeast autolysate or yeast extract is less than 10%, preferably less than 6%, more preferably less than 5% or less than 4% based on the NaCl free dry matter of the yeast autolysate or yeast extract.

The yeast hydrolysate of the second aspect of the invention may be a yeast extract or yeast autolysate as defined hereinbefore. The yeast may be any suitable yeast and is preferable selected from the genera *Saccharomyces, Brettanomyces, Kluyveromyces, Candida* or *Torula*, preferably the genus *Saccharomyces*, more preferably *Saccharomyces cerevisiae* as is used as a baker's yeast or the brewer's yeast *Saccharomyces carlsbergensis* or its synonym *Saccharomyces pastorianus* as is used in the brewing industry for instance to produce lager beer. In a preferred embodiment the yeast is a brewer's yeast and more preferably a spent brewer's yeast which is a side product of the beer brewing process.

In a third aspect the invention provides the use of the yeast hydrolysate or the use of the yeast extract or a yeast autolysate of the second aspect of the invention in a process flavour reaction, in meat applications, or as a flavour enhancer, or as a flavour improver, or in a top note carrier or in a table-top application.

In a fourth aspect the invention provides a flavour enhancer, a meat product, a flavour improver, a top-note carrier or a table-top application which comprises the yeast hydrolysate or the yeast extract or the yeast autolysate of the second aspect of the invention.

Materials and Methods

Gluten Determination

The amount of gluten in the yeast hydrolysate was determined by UPEX-extraction (Universal Prolamin and Glutelin Extractant solution) of the gluten/gliadin and quantifying by an ELISA-test essentially as described by M. C. Mena et al. Talanta 91 (2012) pp 33-40 *"Comprehensive analysis of gluten in processed foods using a new extraction method and a competitive ELISA based on the R5 antibody"*.

The gluten extraction procedure is based on reducing Tris (2-carboxyethyl)-phosphine (TCEP) (Sigma-Aldrich art nr.: C4706, The Netherlands) and anionic surfactant N-lauroylsarcosine (Sarkosyl) (Sigma-Aldrich art nr.: 61745, The Netherlands) reagents in PBS (Sigma-Aldrich art nr.: P3813, The Netherlands).

1. 250 mg dry yeast hydrolysate was weighed and transferred to a 10-ml polypropylene tube.

2. 2.5 ml UPEX solution (5 mM TCEP, 2% N-lauroylsarcosine in PBS, pH 7) was added to the tube containing the yeast hydrolysate. In order to prevent inactivation of the reducing agent, UPEX solution was prepared immediately before use.

3. The tubes were closed tightly and the caps were covered with film to avoid evaporation.

4. The contents of the tubes were mixed thoroughly by vortexing for 5 to 10 seonds and the tubes were placed in a rack.

5. The tubes were incubated in a GL water bath type: 1003 at 50° C. for 40 minutes.

6. The tubes were allowed to cool for 5 min at room temperature.

7. 7.5 ml of 80% ethanol/water (v/v) was added and the samples were thoroughly dispersed by vortexing for 10-60 seconds until total dispersion of the sample was achieved and then incubated for 1 h at room temperature in a rotary (head-overhead) shaker (Stuart Scientific Rollermixer type: SRT2) at 45 turns/min.

8. The tubes were centrifuged in a bench-top centrifuge (Eppendorf model 5810R) for 10 min at 2500 g at room temperature.

9. Using fresh Pasteur pipettes, the supernatant from each tube was transferred to a clean 10-ml polypropylene tube.

10. The solution was analysed by the ELISA test within 24 h of extraction.

For the ELISA test the Ridascreen® Gliadin Competitive kit supplied by R-Biopharm) was used (R-Biopharm AG, Darmstadt, Germany).

EXAMPLES

Example 1

Reduction of Gliadin

Spent brewer's cream yeast was sourced from a brewery in the Netherlands. The obtained yeast was heated to 55° C. and the pH was set to 5.3. Alcalase® (Alcalase® contains the endoprotease subtilisin Carlsberg of *Bacillus licheniformis* and is produced by Novozymes, Denmark and purchased from Sigma, catalogue number P4860) was added to the slurry at a 1% w/w dosage on yeast salt free dry matter. The suspension was incubated overnight. After Alcalase® incubation the suspension was set to pH 5.3 and divided into 4 different fractions. A proline-specific endoprotease was dosed in a range of 0 to 0.5% w/w on salt free dry matter, according to table 1. The suspensions were maintained at 61° C. and incubated for 15 hours. After incubation the suspensions were heated to stop residual enzyme activity. Samples of the suspensions and extracts (after clarification of suspensions) were taken and concentrated by evaporation. The concentrates were analysed for gliadin content by means the UPEX extraction and ELISA test as described in the Materials and Methods.

TABLE 1

| Dose-effect of proline-specific endoprotease | |
|---|---|
| Sample | Gliadin content ppm on total dry matter (w/w) |
| Suspension, no enzyme dosage | 170 |
| Suspension, 0.05% w/w enzyme dosage | 20 |
| Suspension, 0.25% w/w enzyme dosage | <20 |
| Suspension, 0.50% w/w enzyme dosage | <20 |
| Extract, no enzyme dosage | 220 |

TABLE 1-continued

Dose-effect of proline-specific endoprotease

| Sample | Gliadin content ppm on total dry matter (w/w) |
|---|---|
| Extract, 0.05% w/w enzyme added | 25 |
| Extract, 0.25% w/w enzyme added | <20 |
| Extract, 0.50% w/w enzyme added | <20 |

Example 2

Reduction of Gliadin

A brewer's yeast extract (EXPRESA 2200S, DSM FOOD SPECIALTIES, Delft, The Netherlands) in powder formulation was dissolved in water to 10% w/w. The pH of the solution was set to 5.3 and the temperature was maintained at 61 degrees centigrade. The sample was divided into two fractions.

A proline-specific endoprotease was added to one of the 2 flasks containing the yeast extract and was dosed at 0.5% w/w on salt free yeast dry matter. The solution was incubated for 15 hours. After incubation the solution was heated to 90° C. to stop residual enzyme activity. The obtained solution was concentrated by evaporation of water. A concentrated sample was used were analysed for gliadin content by means the UPEX extraction and ELISA test as described in the Materials and Methods.

TABLE 2

Effect of proline-specific endoprotease

| Sample | Gliadin content ppm on total dry matter (w/w) |
|---|---|
| Control (without enzyme) | 200 |
| 0.5% w/w proline-specific endoprotease | <20 |

Example 3

Reduction of RNA of Proline-Specific Endoprotease Compared with Proteases

In this example the undesired degradation of RNA after reducing the gliadin content with proline-specific endoprotease is compared with treatment with commercially available proteases which are also suitable for reduction of gliadin content. A brewer's yeast acquired from a Dutch brewery was used to produce a nucleotide containing yeast autolysate with a high yeast solubilisation yield. Yeast RNA was measured and was 3.4% on dry matter. Firstly, the yeast was heat shocked 5 min at 95° C. Dry matter was subsequently dissolved by two protease steps. First Alcalase® (Alcalase® contains the endoprotease subtilisin Carlsberg of *Bacillus licheniformis* and is produced by Novozymes, Denmark and purchased from Sigma, catalogue number P4860) was incubated at pH 8 and a temperature of 62° C. during 6 hours (dosage:0.8% on dry matter). For the second protease treatment several different enzymes were tested:
Proteax (available from Amano Enzyme)
Peptidase R (available from Amano Enzyme)
Accelerzyme (available from DSM)
Sumizyme FP (available from Shin Nihon)
proline-specific endoprotease (Brewers Clarex, from DSM)

These proteases were separately applied in different experiments (1% on dry matter) and incubated at a pH of 5.2, with a temperature of 51.5° C. during 15 hours. After these two protease steps the enzymes were inactivated by 85° C. heat shock. RNA was converted by incubation with 5'-phosphodiesterase (DSM) and deaminase (Amano) to produce 5'GMP and 5'IMP. The incubation was at pH 5.3 and temperature at 60° C. during 15 hours. After these different processes the amount of 5'-GMP and 5'-IMP in the samples (expressed as weight percentage of the disodium heptahydrate thereof based on sodium chloride free dry matter) were subsequently determined by means of HPLC according to the following method. 5'-GMP and 5'-IMP were quantified by HPLC using a Whatman Partisil 10-SAX column, a phosphate buffer pH 3.35 as eluent and UV detection. Concentrations were calculated on basis of 5'-GMP and 5'-IMP standards. Sodium chloride was determined by measuring the chloride ions in the sample with a Jenway chloride meter PCLM 3 (Jenway, Essex, England) and calculating the corresponding amount of sodium chloride.

The effectiveness of the proteases was measured by determination of solubilisation yield and degree of hydrolysis of the protein. The results are summarized in table 3:

TABLE 3

| Applied enzyme for second protease step | 5'GMP (2Na7H$_2$O in autoloysate on dm) (%) | 5'IMP (2Na7H$_2$O in autoloysate on dm) (%) | Solubilisation yield[1] (%) | Degree of hydrolysis protein[2] (%) |
|---|---|---|---|---|
| Accelerzyme | 0.48 | 0.4 | 55 | 26 |
| Proteax | 0.08 | 0.25 | 59 | 47 |
| Validase FP | 0 | 0 | 64 | 34 |
| Peptidase R | 0.59 | 0 | 64 | 29 |
| Brewers clarex | 0.9 | 1.0 | 60 | 14 |
| Expected | 1.0 | 1.1 | | |

[1]Calculated by DM supernatant/DM broth
[2]Calculated by Free amino acids/total amino acids after acid hydrolysis measured by HPLC Table 3 shows that using a proline-specific endoprotease provides at least 90% 5'-GMP and 5'-IMP of the expected amount 5'-GMP and 5'-IMP, given the RNA content of the starting yeast (3.4%). Thus the proline-specific endoprotease is able to reduce gluten as shown in example 1 and 2, while the RNA present in the yeast is not degraded and thus available to be converted into 5'-ribonucleotides like 5'-GMP and 5'-IMP. This is surprising in view of the amount of 5'-GMP and 5'-IMP for the other proteases which apparently also degraded the RNA of the yeast.

The invention claimed is:

1. A process for preparing a yeast hydrolysate wherein the process comprises the step of contacting a gluten-containing yeast hydrolysate with a proline-specific endoprotease resulting in a yeast hydrolysate comprising less than 100 ppm gluten and at least 1 ppm gluten based on salt-free yeast dry matter.

2. The process according to claim 1 wherein the resulting yeast hydrolysate comprises less than 50 ppm gluten based on salt-free yeast dry matter.

3. The process according to claim 1 wherein the proline-specific endoprotease is classified as EC 3.4.21.26.

4. The process according to claim 1 wherein the proline-specific endoprotease is of a mammalian or a plant or a microbial, origin.

5. The process according to claim 1 wherein the proline-specific endoprotease is a fungal proline-specific endoprotease from a *Penicillium* species or from an *Aspergillus* species.

6. The process according to claim 1 wherein the proline-specific endoprotease is from *Aspergillus niger*.

7. The process according to claim 1 wherein the yeast hydrolysate is a yeast extract or yeast autolysate.

8. The process according to claim 1 wherein the yeast hydrolysate is a spent brewer's yeast hydrolysate.

9. The process according to claim 1, wherein the yeast is a species from the genera *Saccharomyces, Brettanomyces, Kluyveromyces, Candida* or *Torula*.

10. The process of claim 9, wherein the yeast is a species from the genus *Saccharomyces*.

11. The process according to claim 1 wherein the resulting yeast hydrolysate comprises less than 40 ppm based on salt-free yeast dry matter.

12. The process according to claim 1 wherein the resulting yeast hydrolysate comprises less than 30 ppm based on salt-free yeast dry matter.

13. The process according to claim 1 wherein the resulting yeast hydrolysate comprises less than 20 ppm gluten based on salt-free yeast dry matter.

* * * * *